United States Patent
Sobotta et al.

(10) Patent No.: US 6,610,849 B2
(45) Date of Patent: Aug. 26, 2003

(54) PROCESS FOR THE MANUFACTURE OF TROPENOL

(75) Inventors: Rainer Sobotta, Ingelheim (DE); Armin Rapp, Bingen-Dromersheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/160,702

(22) Filed: Jun. 3, 2002

(65) Prior Publication Data

US 2003/0022917 A1 Jan. 30, 2003

Related U.S. Application Data

(60) Provisional application No. 60/305,106, filed on Jul. 13, 2001.

(30) Foreign Application Priority Data

Jun. 28, 2001 (DE) .......................... 101 31 200

(51) Int. Cl.[7] .......................... C07D 451/06
(52) U.S. Cl. ................................ 546/127
(58) Field of Search ................... 546/127

(56) References Cited

PUBLICATIONS

Bremner, "Alkaloids as Starting Materials, etc" ACGC Chem. Res. Communications, 11, 2000, pp 20–28.*
Nicholas S. Aberle et al; Parallel Modification of Tropane Alkaloids, Tetrahedron Letters 42, (2001) pp 1975–1977.
John S. Bremer, et al: A Meisenheimer Rearrangement Approach to Bridgehead Hydroxylated Tropane Alkaloid Derivatives, Tetrahedron Letters vol. 37, No. 1, pp 97–100, 1996.
Chemical Abstract 88:191188—CAPLUS, J. Am. Chem. Soc. 1978, 100, 6.
John R. Malpass, et al; Synthesis of Epitatidine Homologues: Homoepibatidine and Bis–Homoepibatidine, Tetrahedron Letters, vol. 37, No. 22 pp 3911–3914, 1996.

* cited by examiner

*Primary Examiner*—Patricia L. Morris
(74) *Attorney, Agent, or Firm*—Robert P. Raymond; Timothy X. Witkowski; Mary-Ellen Devlin

(57) ABSTRACT

A process for preparing tropenol (I)

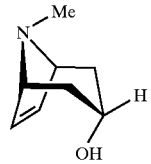

or an acid addition salt thereof, the process comprising:

(a) reducing a scopine ester of formula (II)

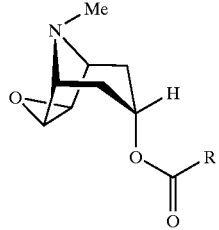

wherein

R is $C_1$–$C_4$-alkyl or $C_1$–$C_4$-alkylene-phenyl, each optionally substituted by hydroxy or $C_1$–$C_4$-alkoxy, or an acid addition salt or hydrate thereof, using zinc in a suitable solvent in the presence of an activating metal salt; and (b) saponifying the product of (a) using a suitable base to obtain the tropenol of formula (I) or the acid addition salt thereof.

16 Claims, No Drawings

PROCESS FOR THE MANUFACTURE OF TROPENOL

RELATED APPLICATIONS

Benefit under 35 U.S.C. §119(e) of prior provisional application Serial No. 60/305,106, filed Jul. 13, 2001, is hereby claimed. Provisional application Serial No. 60/305,106, is also hereby incorporated by reference herein in its entirety.

FIELD OF THE INVENTION

The invention relates to a production method, particularly suitable for use on an industrial scale, for producing tropenol, optionally in the form of the acid addition salts thereof.

BACKGROUND OF THE INVENTION

The compound tropenol is known from the prior art and has the following chemical structure:

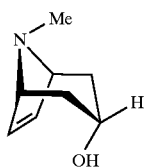
(I)

The compound may be used as a starting compound for preparing pharmacologically useful compounds. For example, in this context, mention may be made of the compounds tiotropium bromide, ipratropium bromide, or BEA2108. These pharmacologically useful structures are characterized by the following chemical structures:

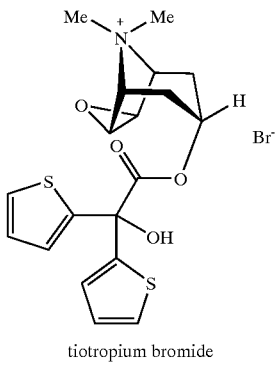
tiotropium bromide

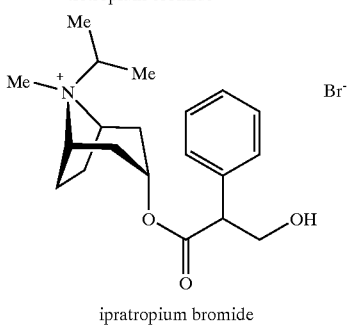
ipratropium bromide

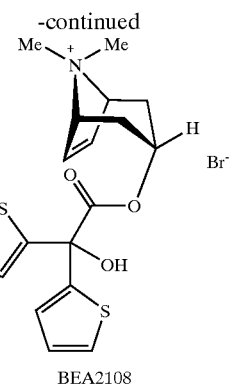
BEA2108

Because of the high potency of the abovementioned compounds, it is necessary to make them available in the purest possible form by efficient methods of synthesis. In particular the high purity requirement, which generally has to be satisfied by compounds for therapeutic use, demands the lowest possible level of contaminants in the starting compounds. When materials which contain a relatively high proportion of impurities are used as starting compounds, the purification of the end product is often difficult, as any impurities introduced initially often cannot easily be removed at later stages of the synthesis except with major losses of yield. This is particularly true when the by-products and contaminants occurring differ only slightly in structure from the main products.

Against this background the aim of the present invention is to provide a method of synthesis which enables tropenol to be produced on an industrial scale, preferably in the form of one of the acid addition salts thereof, in a good yield and, above all, in highly pure form.

DETAILED DESCRIPTION OF THE INVENTION

The objective defined above is achieved by means of the invention described hereinafter.

The present invention accordingly relates to an industrial process for preparing tropenol of formula (I)

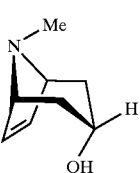
(I)

optionally in the form of the acid addition salts thereof, characterized in that scopine esters of formula (II)

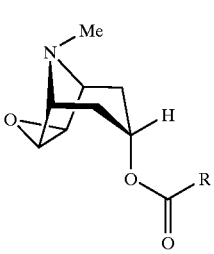
(II)

wherein:

R denotes a group selected from $C_1$–$C_4$-alkyl and $C_1$–$C_4$-alkylene-phenyl, which may be substituted in each case by hydroxy or $C_1$–$C_4$-alkoxy, optionally in the form of the acid addition salts thereof and optionally in the form of the hydrates thereof, in a suitable solvent using zinc in the presence of activating metal salts, preferably activating iron or copper salts, are reduced and subsequently saponified using suitable bases to form tropenol of formula (I).

$C_1$–$C_4$-alkyl within the scope of the present invention denotes branched or unbranched alkyl groups with up to 4 carbon atoms. Methyl, ethyl, n-propyl, isopropyl, n-butyl, sec-butyl, isobutyl and tert-butyl may be mentioned by way of example. $C_1$–$C_4$-alkylene-phenyl, for the purposes of the present invention, denotes phenyl which is linked to up to 4 carbon atoms via a branched or unbranched alkylene bridge. Benzyl, phenyl-2-ethyl, phenyl-1-ethyl, phenyl-3-propyl, phenyl-2-propyl-, etc. may be mentioned by way of example. Both the $C_1$–$C_4$-alkyl groups and the $C_1$–$C_4$-alkylenephenyl groups may, unless otherwise stated, be substituted by one or more hydroxy and/or $C_1$–$C_4$-alkyloxy groups.

Preferably, the present invention relates to a process for preparing tropenol of formula (I), optionally in the form of the acid addition salts thereof, characterized in that scopolamine of formula (II')

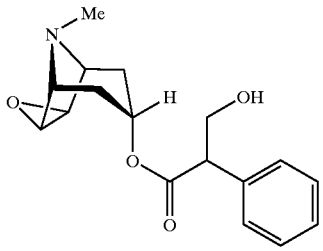

(II')

is used as the scopine derivative of formula (II), optionally in the form of the acid addition salts thereof as well as optionally in the form of the hydrates thereof.

According to the invention, the following procedure may be used to perform the process for preparing tropenol.

The solvent is preferably placed under an inert gas atmosphere, more preferably under nitrogen, in a suitable reaction vessel. Suitable solvents according to the invention include alcohols selected from among methanol, ethanol, and isopropanol or water, while it is preferable according to the invention to use water. According to the invention, between 0.25 L and 5 L, preferably between 0.5 L and 3 L, most preferably between 0.75 L and 1.5 L of solvent are used per mole of the compound of formula (II) used. Zinc, preferably in the form of zinc powder, more preferably zinc powder with an average particle size of <80 µm, most preferably <70 µm is added to the solvent with vigorous stirring. It is essential to use at least 1 mol of zinc per mole of the compound of formula (II) used. According to the invention, zinc is preferably used in an excess. Preferably, 1.2 mol to 3.5 mol, more preferably 1.5 mol to 3.0 mol of zinc are used per mole of the compound of formula (II) used. In a particularly preferred embodiment of the process according to the invention, 1.8 mol to 2.5 mol of zinc are used per mole of the compound of formula (II) used. After the zinc has been added, it may be necessary to activate it. This can be done by adding HI, HBr, or HCl, for example.

Preferably, HI is used as the activating agent, preferably in the form of aqueous solutions, most preferably in the form of concentrated aqueous solutions. It may be necessary, for example, to add 0.05 mol to 0.25 mol, preferably from 0.08 mol to 0.2 mol, of activating agent per mole of the compound of formula (II) used. It may possibly be helpful to increase the temperature of the initial mixture before the activating reagent is added. The mixture is then preferably heated to a temperature of over 50° C., preferably 55° C. to 90° C., particularly preferably 60° C. to 80° C. Then the metal salts are added to the suspension of zinc in the solvent used, optionally activated by means of one of the abovementioned agents. Examples of metal salts which may be used within the scope of the present invention include salts of iron (preferably Fe(III) salts) or copper (preferably Cu(II) salts), preferably the halides thereof. $FeCl_3$ is preferably used as the iron salt. However, it is particularly preferred, within the scope of the process according to the invention, to use Cu(II) salts which are selected from among $CuCl_2$, $CuI_2$, $CuBr_2$, and $CuBr_2$-dimethylsulfide complex, while $CuBr_2$ is particularly important according to the invention. Substoichiometric amounts of the metal salt, preferably 0.01 mol to <1 mol of metal salt, are always added per mole of the compound of formula (II) used according to the invention. Preferably, 0.05 mol to 0.5 mol, most preferably 0.075 mol to 0.2 mol of metal salt are used per mole of the starting compound (II) used. The metal salt may be added to the zinc suspension in bulk or in dissolved form. According to the invention, the metal salt is preferably taken up in one of the solvents mentioned above and then added to the zinc suspension in dissolved or suspended form. It is particularly preferred when preparing the metal salt solution or suspension to use the solvent which is already being used to absorb the zinc. According to the invention, 0.5 L to 1.5 L, preferably 0.6 L to 1.0 L, of solvent are used per mole of the metal salt used to prepare the metal salt solution or suspension. This solution or suspension is then added to the initial zinc mixture with stirring.

The compound of formula (II) is then added to the zinc mixture which may be obtained by the method described hereinbefore. It may optionally be added in the form of the acid addition salts of the compound of formula (II). These acid addition salts are preferably selected according to the invention from the group comprising hydrochloride, hydrobromide, hydrogen phosphate, hydrogen sulfate, tetrafluoroborate, and hexafluorophosphate, of which the hydrochlorides or hydrobromides are particularly preferred. Any reference to acid addition salts of the compound of formula (II) also includes a reference to their hydrates, if any. When the acid addition salts mentioned above are added directly, they may be added to the initial zinc mixture in substance or in dissolved form. If the acid addition salts are added in dissolved form, it is advisable to take up the acid addition salts of the compounds of formula (II) in one of the solvents mentioned above. Preferably, the solution is prepared using the solvent which has already been used to generate the zinc suspension.

According to the invention 0.5 L to 1.5 L, preferably 0.6 L to 1.0 L, of solvent are preferably used per mole of the acid addition salt of formula (II) used.

Alternatively, it is possible to convert the compounds of formula (II) in the form of their free bases into the dissolved acid addition salts by means of the corresponding acids in a separate test setup, initially in a suitable solvent, and then to add this solution to the initial zinc mixture. In this case, one of the abovementioned solvents may be used as the solvent. Preferably, the solvent which has already been used to prepare the initial zinc suspension is used. According to the invention, 0.5 L to 1.5 L, preferably 0.6 L to 1.0 L, of solvent are preferably used per mole of the free base of formula (II) used. The resulting suspension is then combined with the corresponding acid needed to form the acid addition salt, namely the hydrochloride, hydrobromide, hydrogen phosphate, hydrogen sulfate, tetrafluoroborate, or hexafluorophosphate. At least 1 mol of the acid in question is used per mole of the free base of formula (II) used. However, within the scope of the process according to the invention, it is certainly possible to use the acid in excess (i.e., 1.1 mol to about 2 mol per mol of base (II)). According to the invention, the hydrochlorides or hydrobromides of the compounds (II) are preferably used. The hydrochloric acid may be added either in the form of an aqueous solution or in gaseous form, preferably in the form of an aqueous solution. Preferably, concentrated hydrochloric acid (36%) dissolved in water is added. If, as is particularly preferred according to the invention, hydrobromic acid is used, this may also be added either in the form of an aqueous solution or in gaseous form, preferably in the form of an aqueous solution. Preferably, concentrated hydrobromic acid (62%) dissolved in water is added. By adding one of the abovementioned acids to the suspension of the free base of formula (II) in the solvent in question, the pH is adjusted to 3.5 to 5.5, preferably 4.5 to 5.

The solution of the acid addition salts of formula (II) described above and optionally obtainable by various methods is then added to the initial zinc suspension. However, it may also if necessary be added at elevated temperature, for example. The use of an elevated temperature is particularly advisable if the mixture has already been heated before the addition of the activating reagent. If the addition takes place at elevated temperature, temperatures of above 50° C., preferably 55° C. to 90° C., most preferably 60° C. to 80° C., are appropriate according to the invention.

After the addition has ended, the reaction mixture is stirred at a temperature in the range from 50° C. to 100° C., preferably 60° C. to 95° C., most preferably at about 70° C. to 85° C. Depending on the choice of solvent, the maximum temperature mentioned in the above temperature ranges may naturally be lower if the solvent used boils at a temperature which is below the maximum temperature specified. Stirring is continued at a constant temperature until the reaction is complete (0.5 to 4 hours). The progress of the reaction may be monitored for example by thin layer chromatography.

After the reaction has ended, the reaction mixture is combined with a suitable base in order to saponify the ester function. Suitable bases are, preferably, inorganic bases selected from among the alkali or alkaline earth metal carbonates, alkali or alkaline earth metal alkoxides, and alkali or alkaline earth metal hydroxides. Particularly preferred are the hydroxides of lithium, sodium, potassium, and calcium, most preferably sodium or calcium. According to the invention, it is particularly preferred to use sodium hydroxide as the base. The abovementioned bases may be used in pure form or, more preferably, in the form of aqueous concentrated solutions. If, for example, sodium hydroxide is used as the base, which is particularly preferred according to the invention, it is preferably added in the form of an aqueous solution in a concentration of at least 40 wt. %. At least stoichiometric amounts of base have to be used per mole of the compound of formula (II) originally used. However, it is also possible to use the base in excess. Either the base is added at a temperature in the range from 0° C. to 50° C., preferably from 10° C. to 40° C., most preferably at about 20° C. to 30° C., or the above temperature is adjusted immediately after the addition of the base. Stirring is continued at this temperature until conversion is complete (12 hours to 24 hours, depending on the size of the mixture). With smaller batch sizes (e.g., on the kilogram scale) saponification can also be carried out at elevated temperature (50° C. to 100° C., preferably 55° C. to 90° C., most preferably about 60° C. to 80° C.). In this way, the reaction time can be shorted to about 15 minutes to 10 hours, preferably 0.5 to 3 hours. The progress of the reaction may be monitored, for example, by thin layer chromatography.

After the reaction is complete, the reaction is brought to a temperature in the range from 0° C. to 50° C., preferably 15° C. to 45° C., with stirring and the zinc salts are eliminated by filtration. The filter residue may optionally be washed with the solvent used for the reaction. For extraction, the filtrate is combined with an organic solvent which is immiscible to only slightly miscible with the solvent chosen for the reaction. Preferably, an organic solvent selected from among methyl tert-butyl ether, dichloromethane, and chloroform, preferably dichloromethane, is used. According to the invention, between 0.5 L and 5 L, preferably between 0.75 L and 4 L, of organic solvent are used for the extraction per mole of the compound of formula (II) used. The extraction is carried out according to the invention between 3 and 8 times, preferably 4 to 6 times. After extraction has ended, the organic phases are combined and the organic solvent is distilled off in vacuo.

The crude product remaining is taken up in an organic solvent selected from among methanol, ethanol, and isopropanol, preferably isopropanol. According to the invention, between 0.1 L and 2.0 L, preferably between 0.3 L and 1.0 L of this abovementioned solvent are used per mole of the compound of formula (II) originally used. The solution obtained is separated from the precipitated solid (metal salts of the acid RCOOH, where R may have the meanings given hereinbefore) by filtration. The filtrate contains tropenol of formula (I) in the form of its free base. If the free base is to be used in the next reaction, the solvent is distilled off in vacuo at this point. The remaining free base can then be used in the next steps of the synthesis, without further purification. According to the invention, however, the free base of tropenol is preferably converted into one of the acid addition salts. By the acid addition salts of tropenol are meant, for the purposes of the present invention, the salts selected from among the hydrochloride, hydrobromide, hydrogen phosphate, hydrogen sulfate, tetrafluoroborate, or hexafluorophosphate. The hydrobromide and hydrochloride salts are particularly preferred, while tropenol hydrochloride is of particular importance according to the invention. To prepare the acid addition salts, the filtrate is cooled to a temperature in the range from −10° C. to 20° C., preferably in the range from −5° C. to 15° C. The suspension thus obtained is then combined with the corresponding acid needed to form the acid addition salts, namely the hydrochloride, hydrobromide, hydrogen phosphate, hydrogen sulfate, tetrafluoroborate, or hexafluorophosphate. At least 1 mol of the acid in question should be used per mole of the free base of formula (II) originally used. It may be possible, within the scope of the processes according to the invention, to use the acid in excess (i.e., 1.1 mol to about 2 to 3 mol per mole of the base (II) originally used). According to the invention the hydrochloride of tropenol is preferably prepared. The hydrochloric acid required for this may be added either in the form of a solution or in gaseous form. Preferably, hydrogen chloride in gaseous form is added to one of the abovementioned solvents in a separate reaction vessel until saturation point is reached. Most preferably, this HCl solution is prepared using the solvent which was used to prepare the tropenol filtrate. One of the abovementioned acids is added to the solution of the free base of the tropenol (I) until a pH of 1.5 to 6.5, preferably 2 to 6, is obtained. After all the acid has been added, stirring may optionally continue at constant temperature for a further 0.5 to 2 hours. Finally, the precipitated acid addition salt of tropenol is separated off and optionally washed with a solvent selected from among acetone, methyl isobutyl ketone, and methyl ethyl ketone, preferably acetone, and dried in vacuo.

As mentioned in the introduction, tropenol, which may be obtained by the preparation process according to the invention, is a valuable starting compound for preparing therapeutically active compounds such as, for example, tiotropium bromide, ipratropium bromide, or BEA2108. Because of the high purity in which tropenol can be obtained according to the present invention, it is possible to prepare the abovementioned active substances in the specifications required for pharmaceutical use.

Accordingly, the present invention further relates to the use of tropenol, optionally in the form of the acid addition salts thereof, as a starting material for preparing therapeutically active compounds such as for example tiotropium bromide, ipratropium bromide, or BEA2108, preferably tiotropium bromide.

Moreover, the present invention relates to the use of compounds of formula (II)

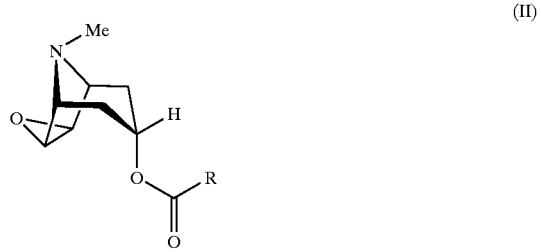

wherein:
R denotes a group selected from $C_1$–$C_4$-alkyl and $C_1$–$C_4$-alkylene-phenyl which may be substituted in each case by hydroxy or $C_1$–$C_4$-alkoxy,
optionally in the form of the acid addition salts thereof as well as optionally in the form of the hydrates thereof, as a starting material for preparing therapeutically active compounds such as, for example, tiotropium bromide, ipratropium bromide, or BEA2108, preferably tiotropium bromide.

Preferably, the present invention relates to the use of scopolamine, optionally in the form of the acid addition salts thereof and optionally in the form of the hydrates thereof, as a starting material for preparing therapeutically active compounds such as, for example, tiotropium bromide, ipratropium bromide, or BEA2108, preferably tiotropium bromide.

The procedure illustrated in Diagram 1 may be used to prepare tiotropium bromide starting from tropenol.

Diagram I

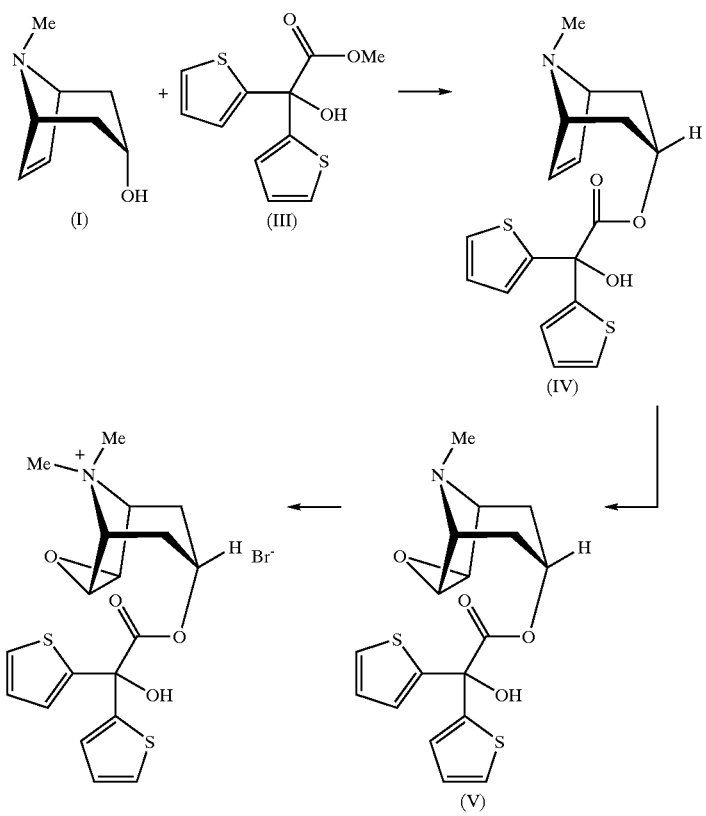

Starting from the tropenol (I) which may be obtained according to the invention, first tropenol di-(2-thienyl)- glycolate (IV) is formed by reacting with di-(2-thienyl)-glycolic acid derivatives (III). This ester is converted by oxidation of the olefinic double bond into the corresponding scopine ester (V), from which tiotropium bromide can be obtained by reacting with methyl bromide.

Therefore, in a particularly preferred aspect, the present invention relates to a process for preparing tiotropium bromide

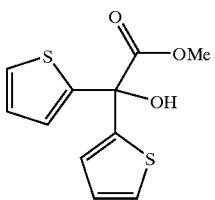

characterized in that in a first step a scopine ester of formula (II)

(II)

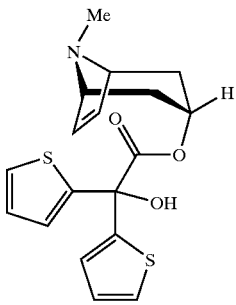

wherein:

R denotes a group selected from $C_1$–$C_4$-alkyl and $C_1$–$C_4$-alkylene-phenyl which may be substituted in each case by hydroxy or $C_1$–$C_4$-alkoxy, is reduced, optionally in the form of the acid addition salts thereof, using zinc in a suitable solvent in the presence of activating metal salts, preferably activating iron or copper salts, and simultaneously saponified using suitable bases to obtain tropenol of formula (I)

(I)

which is optionally reacted in a second step, in the form of the acid addition salts thereof, with an ester of formula (III)

(III)

to obtain the tropenol ester of formula (IV)

(IV)

and this is oxidized in a third step to form the scopine ester of formula (V)

(V)

which is quaternized with methyl bromide in a fourth step to obtain tiotropium bromide.

The Examples that follow serve to illustrate some methods of synthesis carried out by way of example in order to prepare tiotropium bromide. They are intended solely as possible procedures, provided as an illustration, without restricting the invention to their content.

EXAMPLE 1

Preparation of Tropenol (I) in the Form of its Hydrochloride (on a Kilogram Scale)

3 L of water are placed in a reactor flushed with nitrogen, and 390 g of zinc powder (<63 μm) and, as an activator, 66 mL of 57% aqueous hydriodic acid solution are added with vigorous stirring. This mixture is stirred at ambient temperature for about 5 minutes. Then 67.2 g of Cu(II) bromide, dissolved in 260 mL of water, are slowly added. A solution of 910.2 g of scopolamine base taken up in about 2.6 L of water are slowly added to this mixture and the pH is adjusted to 4.5 to 5 using 227 mL of 62% aqueous hydrobromic acid solution. After the addition has ended, the mixture is heated to a temperature of 75° C. to 80° C. and stirred for about 2 hours at this temperature. After the reaction is complete (monitored by TLC), it is cooled to about 65° C. 480 mL of a 45% aqueous sodium hydroxide solution are added and the mixture is stirred at a temperature of 65° C. to 70° C. until saponification is complete (about 1 hour). After cooling to about 40° C., the Zn salts are filtered off and washed with about 200 mL of water. The filtrate is repeatedly extracted with dichloromethane (3 to 5 times, each time with 2 L to 4 L of dichloromethane), the organic phases are combined and the solvent is distilled off under reduced pressure. The residue remaining (371 g of crude product) is taken up in 1.5 L of isopropanol and the precipitated solid (metal salt of tropic acid) is filtered off. The filtrate is cooled to −10° C. to 10° C. and 120 g of HCl dissolved in 780 mL of isopropanol is slowly added with vigorous stirring. The pH is adjusted to 2.5 to 4. After the addition has ended, the mixture is stirred for another hour at about −5° C. The suspension is finally filtered, the filter residue is washed with about 600 mL of acetone, and lastly dried in vacuo at about 60° C. Yield: 408.1 g of tropenol hydrochloride (77.4% based on the scopolamine used).

EXAMPLE 2

Preparation of Tropenol (I) in the Form of its Hydrochloride (on an Industrial Scale)

130 L of water are placed in a reactor flushed with nitrogen and 21.5 kg of zinc powder (<63 $\mu$m) are added with vigorous stirring. This mixture is heated to a temperature of 65° C. to 75° C. 6.2 kg of 57% aqueous hydriodic acid are added to this mixture. Then a solution of 3.7 kg of Cu(II) bromide in 20 L to 25 L of water is added. The mixture is optionally stirred for up to 5 minutes and then a solution of 65.8 kg of scopolamine-hydrobromide-trihydrate in 140 L to 145 L of water is added. The resulting mixture is heated to 75° C. to 85° C. and stirred for 2 to 2.5 hours. After total conversion (monitored by TLC), 35.5 kg of a 45% aqueous sodium hydroxide solution are added. The mixture is brought to a temperature of 20° C. to 30° C. and stirred for a further 20 to 24 hours. After total conversion (monitored by TLC), the entire contents of the apparatus are filtered and the residue remaining is washed with about 30 L of water. The filtrate is combined with 75 kg of sodium chloride at constant temperature. For extraction, 150 L of dichloromethane are added. The organic phase is separated off and the aqueous phase is extracted a further 4 times with the same amount of dichloromethane. The combined organic phases are freed from solvent by distillation. About 100 L of isopropanol are added to the remaining residue and the temperature is adjusted to 0° C. to 10° C. Then a solution of 5.5 kg of hydrogen chloride in 38 L of isopropanol is added until a pH of about 2.5-5.5 is obtained. The tropenol hydrochloride precipitated is separated off and washed with 30 L of acetone. After drying, 21.3 kg of product (yield: 81% based on the scopolamine hydrobromide used) are obtained.

EXAMPLE 3

Preparation of Tiotropium Bromide a. Preparation of the Tropenol Ester (IV)

Ammonia (1.8 kg) is piped into 10.9 kg of tropenol hydrochloride (obtainable according to Example 1) in toluene (95 L) at 25° C. The resulting suspension is stirred for about 1 hour at constant temperature. Then the ammonium hydrochloride formed is filtered off and rinsed with toluene (26 L). At a jacket temperature of about 50° C., some of the toluene (about 60 L) is distilled off in vacuo. After cooling to about 25° C., 15.8 kg of methyl di-(2-thienyl)glycolate are added and the resulting mixture is heated to 50° C. to dissolve it. Toluene (40 L) is placed in another apparatus and sodium hydride (2.7 kg) is added thereto at about 25° C. The previously formed solution of tropenol and methyl glycolate is added to this solution at 30° C. within 1 hour. After the addition has ended, the mixture is heated to 75° C. under reduced pressure for about 7 hours with stirring. The methanol formed is distilled off. The mixture remaining cooled and added to a mixture of water (958 L) and 36% hydrochloric acid (13.2 kg). The aqueous phase is then separated off and washed with methylene chloride (56 L). After more methylene chloride has been added (198 L), the mixture thus obtained is adjusted to pH 9 with prepared soda solution (9.6 kg of soda in 45 L of water). The methylene chloride phase is separated off and the aqueous phase is stirred with methylene chloride (262 L). The methylene chloride phase is evaporated down to the residue at 65° C. The residue is taken up in toluene (166 L) and heated to 95° C. The toluene solution is cooled to 0° C. The crystals obtained are separated off, washed with toluene (33 L), and dried at about 50° C. for a maximum of 24 hours in a nitrogen current. Yield: 18.6 kg (83%); melting point: about 160° C. (determined by TLC at a heating rate of 10 K/min).

b. Preparation of the Scopine Ester (V)

260 L of DMF are placed in a suitable reaction apparatus and heated to 50° C. Then 16.2 kg of tropenol ester (IV) are added and the mixture is stirred until a clear solution is obtained. After cooling to 40° C., hydrogen peroxide-urea complex (10.2 kg), water (13 L) and vanadium(V) oxide (0.7 kg) are added successively batchwise and the contents of the apparatus are heated to about 50° C. After 2 to 3 hours stirring at constant temperature, the mixture is cooled to about 20° C. The reaction mixture obtained is adjusted to about pH 4.0 with 36% hydrochloric acid. Prepared sodium bisulfite solution (2.4 kg in 24 L of water) is added. At an internal temperature of 35° C., the solvent is partially distilled off in vacuo (about 210 L). It is cooled to about 20° C. again and combined with Clarcel (3.2 kg). The pH is adjusted to about 2.0 with dilute hydrochloric acid (36%, 0.8 kg in about 440 L of water). The resulting solution is filtered and extracted with methylene chloride (58 L). The methylene chloride phase is discarded. Methylene chloride (130 L) is again added to the aqueous phase and the pH is adjusted to about 10.0 with a prepared soda solution (11.0 kg in 51 L of water). The methylene chloride phase is separated off and the aqueous phase is extracted with methylene chloride (136 L). Methylene chloride (about 175 L) is distilled off from the combined methylene chloride phases in a weak vacuum (600 mbar to 700 mbar) at 40° C. The contents of the apparatus are cooled to 20° C., acetyl chloride (about 0.5 kg) is added and the mixture is stirred for about 40 minutes at 20° C. The reaction solution is transferred into a second apparatus. The pH is adjusted to 2.0 with a prepared hydrochloric acid solution (4.7 kg of 36% hydrochloric acid in 460 L of water) at 20° C. The methylene chloride phase is separated off and discarded. The aqueous phase is washed with methylene chloride (39 L). Then methylene chloride (130 L) is added and the pH is adjusted to 10.0 with a prepared soda solution (7.8 kg of soda in 38 L of water) at 20° C. After 15 minutes stirring, the organic phase is separated off and the aqueous phase is washed twice with methylene chloride (97 L and 65 L). The methylene chloride phases are combined and some of the methylene chloride (90 L) is distilled off in a weak vacuum at a temperature of 30° C. to 40° C. Then dimethylformamide (114 kg) is added and the remainder of the methylene chloride is distilled off in vacuo at 40° C. The contents of the apparatus are cooled to 20° C.

c. Preparation of the Tiotropium Bromide

Methyl bromide (5.1 kg) is piped into the scopine ester solution obtained by the method described above at 20° C. The contents of the apparatus are stirred at 30° C. for about 2.5 days. 70 L of DMF are distilled off at 50° C. in vacuo. The solution is transferred into a smaller apparatus. It is rinsed with DMF (10 L). Additional DMF is distilled off at 50° C. in vacuo until a total amount of distillate of about 100 L is obtained. This is cooled to 15° C. and stirred for 2 hours at this temperature. The product is isolated using a suction filter drier and washed with 15° C. cold DMF (10 L) and 15° C. cold acetone (25 L). It is dried at a maximum of 50° C. for a maximum of 36 hours in a nitrogen current. Yield: 13.2 kg (88%); melting point: 200° C.–230° C. (depending on the purity of the starting product).

The crude product thus obtained (10.3 kg) is added to methanol (66 L). The mixture is refluxed to dissolve it. The solution is cooled to 7° C. and stirred for 1.5 hours at this temperature. The product is isolated using a suction filter drier, washed with 7° C. cold methanol (11 L), and dried for a maximum of 36 hours at about 50° C. in a nitrogen current. Yield: 9.9 kg (96%); melting point: 228° C. (determined by TLC at a heating rate of 10 K/min).

If desired the product thus obtained can be converted into the crystalline monohydrate of tiotropium bromide. This may be done as follows.

15.0 kg of tiotropium bromide are added to 25.7 kg of water in a suitable reaction vessel. The mixture is heated to 80° C. to 90° C. and stirred at constant temperature until a clear solution is formed. Activated charcoal (0.8 kg), moistened with water, is suspended in 4.4 kg of water, this mixture is added to the solution containing tiotropium bromide and rinsed with 4.3 kg of water. The resulting mixture is stirred for at least 15 minutes at 80° C. to 90° C. and then filtered through a heated filter into an apparatus which has been preheated to an external temperature of 70° C. The filter is rinsed with 8.6 kg of water. The contents of the apparatus are cooled to a temperature of 20° C. to 25° C. at a rate of 3° C. to 5° C. per 20 minutes. The apparatus is further cooled to 10° C. to 15° C. using cold water and crystallization is completed by stirring for at least one hour. The crystals are isolated using a suction filter drier, the isolated crystal slurry is washed with 9 L of cold water (10° C. to 15° C.) and cold acetone (10° C. to 15° C.). The crystals obtained are dried at about 25° C. over about 2 hours in a nitrogen current. Yield: 13.4 kg of tiotropium bromide-monohydrate (86% of theory); melting point: 230° C. (determined by TLC at a heating rate of 10 K/min).

We claim:

1. A process for preparing tropenol (I)

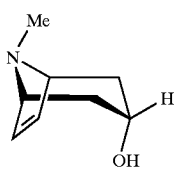

(I)

or an acid addition salt thereof, the process comprising:

(a) reducing a scopine ester of formula (II)

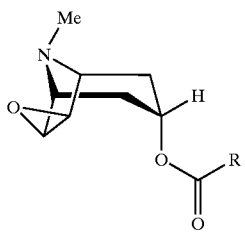

(II)

wherein
R is $C_1$–$C_4$-alkyl or $C_1$–$C_4$-alkylene-phenyl, each optionally substituted by hydroxy or $C_1$–$C_4$-alkoxy,
or an acid addition salt or hydrate thereof, using zinc in a suitable solvent in the presence of an activating metal salt; and (b) saponifying the product of (a) using a suitable base to obtain the tropenol of formula (I) or the acid addition salt thereof.

2. The process according to claim 1, wherein the scopine ester of formula (II) is the scopolamine of formula (II')

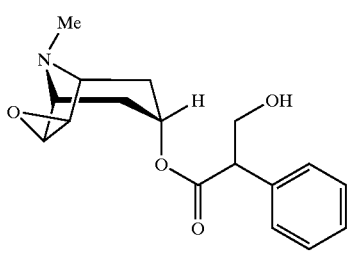

(II')

or an acid addition salt or hydrate thereof.

3. The process according to claim 1, wherein the zinc is used in stoichiometric excess to the scopine ester of formula (II) or the acid addition salt or hydrate thereof.

4. The process according to claim 2, wherein the zinc is used in stoichiometric excess to the scopine ester of formula (II) or the acid addition salt or hydrate thereof.

5. The process according to claim 1, wherein the zinc is activated using an activating agent.

6. The process according to claim 2, wherein the zinc is activated using an activating agent.

7. The process according to claim 5, wherein the activating agent is selected from HCl, HBr, and HI.

8. The process according to claim 6, wherein the activating agent is selected from HCl, HBr, and HI.

9. The process according to one of claims 1 to 8, wherein the suitable base is selected from an alkali or alkaline earth metal carbonate, alkali or alkaline earth metal alkoxide, alkali or alkaline earth metal hydroxide, or an aqueous concentrated solution thereof.

10. The process according to one of claims 1 to 8, wherein the suitable base is selected from lithium hydroxide, sodium hydroxide, potassium hydroxide, calcium hydroxide, or an aqueous concentrated solution thereof.

11. The process according to one of claims 1 to 8, wherein the activating metal salt is an iron salt or a copper salt.

12. The process according to one of claims 1 to 8, wherein the activating metal salt is an iron (II) salt or a copper (II) salt.

13. The process according to one of claims 1 to 8, wherein the activating metal salt is an iron (II) halide salt or a copper (II) halide salt.

14. The process according to one of claims 1 to 8, wherein the activating metal salt is selected from $FeCl_3$, $CuCl_2$, $CuI_2$, $CuBr_2$, and $CuBr_2$-dimethylsulfide complex.

15. The process according to claim 1, wherein the reducing step is accomplished by adding the scopine ester of formula (II) or the acid addition salt or hydrate thereof to a previously prepared zinc-containing solution made by adding the zinc and the metal salt to the suitable solvent.

16. The process according to claim 15, wherein the zinc in the zinc-containing solution is activated with an activating agent before the scopine ester of formula (II) or the acid addition salt or hydrate thereof is added to the zinc-containing solution.

* * * * *

UNITED STATES PATENT AND TRADEMARK OFFICE
CERTIFICATE OF CORRECTION

PATENT NO.    : 6,610,849 B2
DATED         : August 26, 2003
INVENTOR(S)   : Ranier Sobotta et al.

It is certified that error appears in the above-identified patent and that said Letters Patent is hereby corrected as shown below:

<u>Column 14,</u>
Line 18, "a suitable solvent" should read -- water --.

<u>Column 15,</u>
Line 8, "suitable solvent" should read -- water --.

Signed and Sealed this

Twenty-third Day of March, 2004

JON W. DUDAS
*Acting Director of the United States Patent and Trademark Office*